US00PP28202P3

(12) United States Plant Patent
Byrne et al.

(10) Patent No.: US PP28,202 P3
(45) Date of Patent: Jul. 18, 2017

(54) NECTARINE TREE NAMED 'SMOOTH ZEST ONE'

(50) Latin Name: *Prunus persica*
Varietal Denomination: Smooth Zest One

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 109 days.

(21) Appl. No.: 14/544,513

(22) Filed: Jan. 13, 2015

(65) Prior Publication Data

US 2016/0205825 P1 Jul. 14, 2016

(51) Int. Cl.
*A01H 5/08* (2006.01)

(52) U.S. Cl.
USPC ..... Plt./188

(58) Field of Classification Search
USPC ..... Plt./188
See application file for complete search history.

(56) References Cited

PUBLICATIONS

Philips. AgriLife Today, Dec. 30, 2013.*
The Brooks and Olmo Register of Fruit and Nut Varieties, 3rd Ed., American Society of Horticultural Science Press, Alexandria, VA, 1997.
Byrne et al.; 'TexFirst', An early ripening low chill peach for the subtropics; HortScience; 2012; pp. 1803-1804; vol. 47.
Sherman et al.; 'Sunraycer' Nectarine; HortScience; 1995; p. 154; vol. 30(1).

* cited by examiner

*Primary Examiner* — Keith Robinson
(74) *Attorney, Agent, or Firm* — Ramey & Schwaller, LLP

(57) ABSTRACT

Disclosed is a new nectarine variety of *Prunus persica* named 'SMOOTH ZEST ONE'. This new variety, which requires 200-250 chilling units of dormancy, is considered to be a nectarine tree of early season maturity, which ripens in early to mid May in the medium chill zone of Texas and produces white fleshed fruit that are firm, attractively colored, and suitable for both local and regional fresh fruit markets.

4 Drawing Sheets

BACKGROUND OF THE INVENTION

Field of the Invention

This invention relates to nectarine trees and, more specifically, to nectarine trees referred to as a variety of *Prunus persica* named 'Smooth Zest One'. 'Smooth Zest One', which requires 200-250 chilling units of dormancy, produces firm, white-fleshed clingstone nectarine that matures early in the season.

SUMMARY OF THE INVENTION

The 'Smooth Zest One' nectarine is characterized as to novelty and is otherwise noteworthy by requiring little winter chilling (200-250 chilling units) to fruit, and by producing firm, white-fleshed clingstone nectarine fruit that ripens in the early season. In this regard, the present variety of nectarine tree bears fruit that are ripe for commercial harvesting and shipment in the first half of May, when the fruit is grown in the low to medium chill zone of Texas. 'Smooth Zest One' ripens with or slightly before 'Flordaking' (not patented, Andrews et al., 1979) and 5-6 days before 'Smooth Delight One' (U.S. Plant patent application Ser. No. 14/544,508) and 'Smooth Delight Two' (U.S. Plant patent application Ser. No. 14/544,522) in the medium chill zone.

ORIGIN OF THE VARIETY

The present nectarine tree was the result of an ongoing Stone Fruit Breeding Program of Texas A & M University, College Station, Brazos County, Tex. To this end, both controlled and hybrid crosses are made each year to produce seedling populations from which improved progenies are evaluated and selected.

The seedling 'SMOOTH ZEST ONE' (TX2B300WN) was originated at the Texas A & M University Horticultural Farm in College Station, Tex. and was chosen from a population of seedlings that resulted from seed from a cross between an unreleased white fleshed semi freestone peach selection, TX3D75W (not patented) as the female parent, and the low chill peach, 'TexFirst' (U.S. Plant Pat. No. 26,119) as the male parent. TX3D75W was discovered in 1997 in a population derived from a cross with a white peach with unknown parentage and the Florida nectarine 'Sunraycer' (not patented, Sherman et al., 1995). Resulting seed from this TX3D75W×'Sunraycer' were planted in a high density breeding orchard at the Texas A & M University Horticultural Farm in College Station, Tex. in 2004. In 2005, the selection TX2B300WN ('Smooth Zest One') was marked for subsequent observation and noted as having exceptional characteristics.

ASEXUAL REPRODUCTION OF THE VARIETY

'Smooth Zest One' was bud grafted onto virus-free Nemaguard (not patented, Brooks and Olmo, 1997) peach rootstock in June 2004 at the nursery site in Oakdale, Calif. The variety was subsequently planted at the experimental orchard in the central portion of the San Joaquin Valley, near Fowler, Fresno County, Calif. and in two sites in Texas (College Station and Floresville). Fruit from the resulting propagation has been evaluated during the period from 2006 to 2010 fruit seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographs. The fruit, flowers, and shoots photographed were harvested off a 5-year old tree.

BOTANICAL DESCRIPTION OF THE VARIETY

Figure 1:
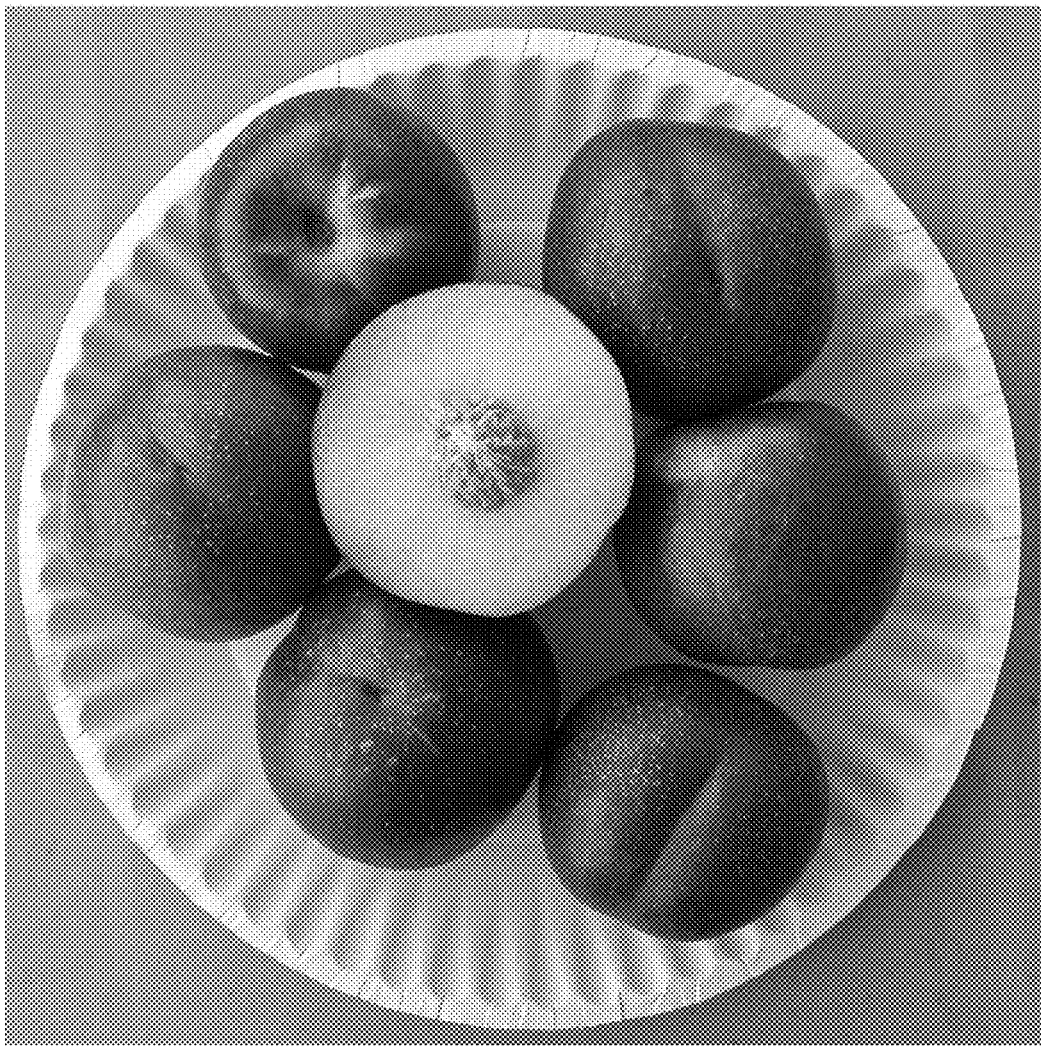
FIG. 1. Fruit of 'Smooth Zest One' showing apical and distal views as well as fruit dissected in the axial plane to illustrate the flesh and stone characteristics.
Figure 2:
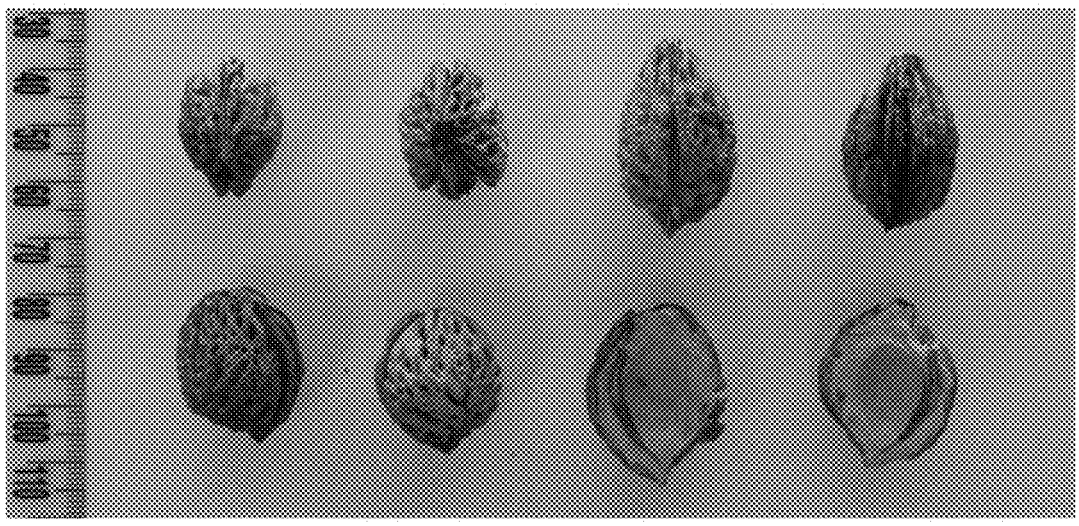
FIG. 2. Dried endocarps of 'Smooth Zest One' showing various views. The ruler is demarcated in millimeters.
Figure 3:
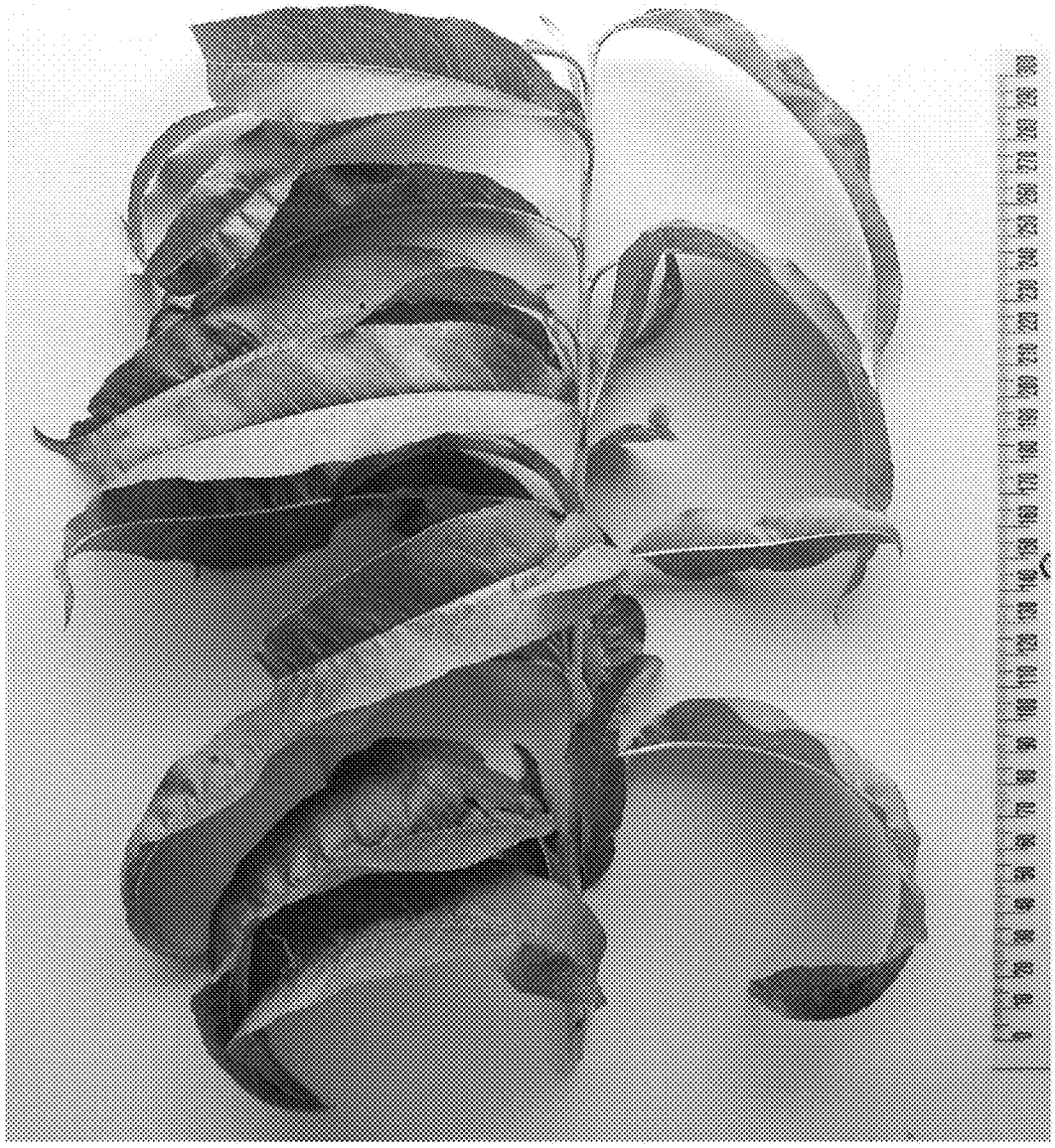
FIG. 3. 'Smooth Zest One' nectarine showing typical leaves and shoots. The ruler is demarcated in millimeters.
Figure 4:
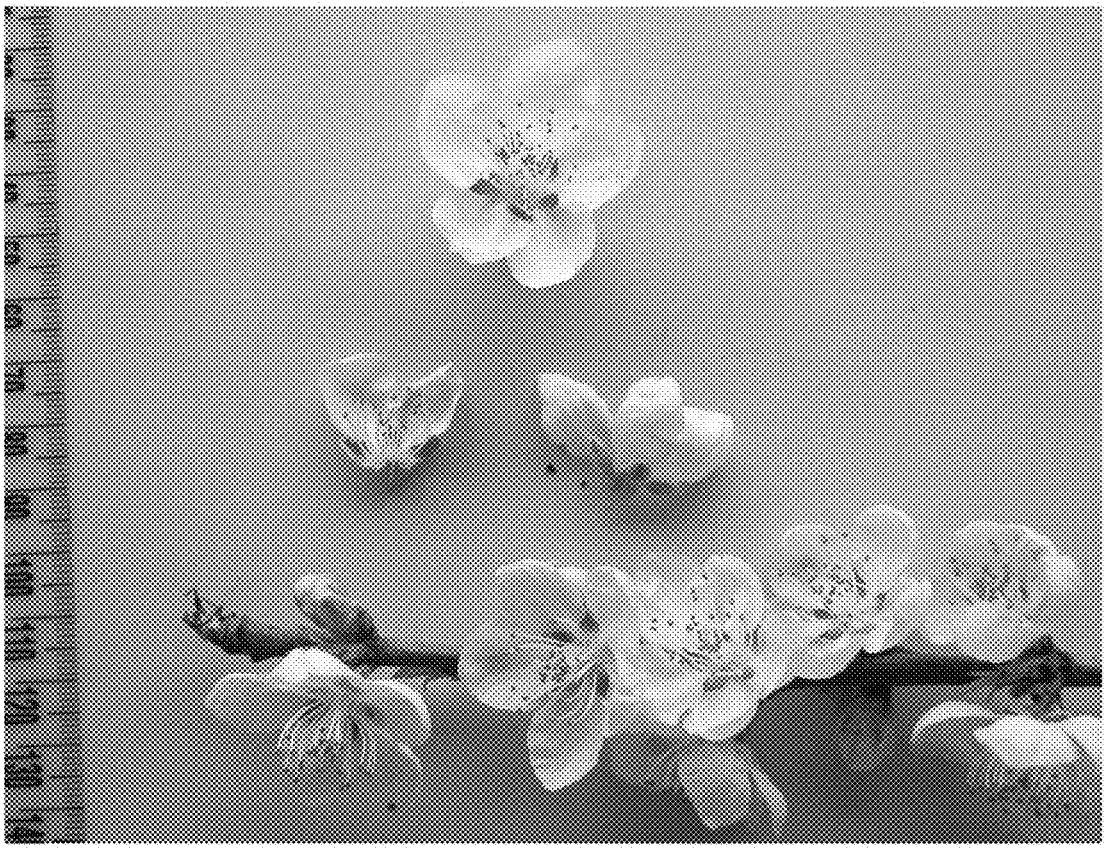
FIG. 4. The showy flowers of 'Smooth Zest One'. The ruler is demarcated in millimeters.

Referring more specifically to the pomological details of this new and distinct variety of nectarine tree, the following has been observed under the ecological conditions prevailing in the low and medium chill zones of Texas. All major color code designations are by reference to The R.H.S. Colour Chart (2001) provided by The Royal Horticultural Society of Great Britain. Colors are approximate as color depends on horticultural practices such as light level and fertilization rate, among others. Descriptions were done on trees that were 5-years old.

Tree:

*Size*.—Generally average to above average as compared to other common nectarine cultivars ripening in the early season of maturity.

*Height*.—8.0 feet (2.44 m) at the end of the 2012 growing season on 5-year old trees.

*Width*.—6.0 feet (1.83 m) at the end of the 2012 growing season on 5-year old trees.

*Vigor*.—High.

*Density*.—Medium to high.

*Productivity*.—Productive.

*Shape*.—The 'Smooth Zest One' exhibits a generally spreading growth habit typical of commercial varieties of peaches such as 'TexKing' (U.S. Plant Pat. No. 14,627) and 'TexRoyal' (not patented, Byrne and Bacon, 1991).

*Current season growth*.—The current season growth for the new variety was approximately 3.0 to 3.7 feet (0.91-1.13 m).

*Regularity of bearing*.—Regular, and considered hardy under typical conditions found in the low to medium chill zones of Texas and in the central San Joaquin Valley, Calif.

Trunk:

*Size*.—Approximately 4.3 inches (10.9 cm) in diameter and 14.8 inches (37.6 cm) in circumference when measured at a distance of approximately 12 inches (30.5 cm) above the soil level, at the end of the 2012 growing season on a five-year old tree.

*Bark texture*.—Considered moderately rough with numerous folds of papery scarf-like skin being present.

*Bark coloration*.—Variable, colors present are 178A-B of the Greyed-Red Group, 197D and 198D of the Greyed-Green Group and N200D of the Brown Group.

Branches:

*Size*.—Considered medium for the variety.

*Thickness and length*.—Average (about 4.5 cm in diameter as measured 10 cm from the trunk on a five-year old tree) as compared to other varieties. The length of the branches are limited by pruning to a 3 to 5 foot (approximately 0.9 to 1.5 m) length depending on its position in the tree.

*Surface texture*.—Average and appearing furrowed on wood that is several years old.

*Lenticels*.—Numerous flat, oval lenticels present. The lenticels range in size from approximately 3.0 to 6.0 mm in width and were approximately 1 mm in height.

*Current season shoots*.—Surface texture — Substantially glabrous.

*Internode length*.—Approximately 3.5 to 5.7 cm as measured in the middle of a current season stem.

*Color of mature branches*.—The predominant colors are 183A-B and 184A of the Greyed-Purple Group, 198D of the Greyed-Green Group and N200D of the Brown Group.

*Current season shoots*.—Color — Medium to light green (141C-D and 143A-C of the Green Group and 144A-C, N144C, 146B-D and 147B of the Yellow-Green Group) with some reddish-brown coloration appearing on exposed surface of the shoots (165A, 166A, 174A, 176A-B and 177A-B of the Greyed-Orange Group; N199B of the Grey-Brown Group and 200A-D of the Brown Group). The color of new shoot tips is considered a bright and shiny green (mainly Green Groups 141C-D and 142A-B). The upper exposed surface of current season shoots exhibit weak to medium intensity of anthocyanins.

Leaves:

*Size*.—Considered moderately large for the species. Leaf measurements have been taken from vigorous upright current season growth approximately at mid-shoot.

*Leaf length*.—Approximately 175 to 180 mm.

*Leaf width*.—Approximately 45 to 49 mm.

*Leaf thickness*.—Less than 1 mm.

*Leaf form*.—Lanceolate.

*Leaf tip form*.—Acuminate.

*Leaf upper surface color*.—Green, approximately 137A of the Green Group.

*Leaf lower surface color*.—Green, approximately 137C-D and 138A of the Green Group.

*Leaf mid-vein color*.—Pale green, approximately 145C-D and 150D Yellow-Green Group.

*Leaf margins*.—

*Form*.—Considered crenate/crenulate.

*Uniformity*.—Considered generally uniform.

*Leaf petioles*.—

*Size*.—Considered medium long.

*Length*.—Approximately 13 to 14 mm.

*Thickness*.—Approximately 1 to 2 mm.

*Color*.—Pale green (approximately Yellow-Green Groups 145B and 149B).

*Leaf glands*.—

*Size*.—Approximately 0.5-1 mm in height and 0.5 mm in width.

*Number*.—Generally 0-2 per leaf.

*Type*.—Reniform.

*Color*.—Brown (N199C of the Grey-Brown Group).

*Leaf stipules*.—

*Size*.—Medium long for the species.

*Length*.—Approximately 10 to 15 mm.

*Width*.—Less than 1 mm.

*Form*.—Lanceolate.

*Color*.—Green (Yellow-Green 144B-C) with reddish brown tips (Greyed-Orange Group 177C-D) when young. The stipules are considered to be early deciduous.

*Ratio of wood (leaf) buds to flowering buds*.—1 to 2 flower buds per vegetative bud.

Flowers:

*Floral buds*.—

*General*.—The floral buds are considered to be medium to medium large in size, conic in form, and slightly appressed relative to the bearing shoot.

*Color*.—The bud scales are a light gray-green color, (approximately Yellow-Green Group 145A-B, Greyed-White Group 156C-D and the Greyed-Purple Group 186A-B). The buds are considered hardy under the typical climatic conditions in the low and medium chill zones of Texas and in central San Joaquin Valley, Calif. climatic conditions.

*Length*.—Approximately 5 to 10 mm.

*Width*.—Approximately 2.5 to 5 mm.

*Blooming type*.—Considered quite early in relation to other nectarine cultivars commonly growing in the central San Joaquin Valley. Date of full bloom was between February 3rd and February 10th during the period between 2008 and 2012 with an average full bloom date of February 6th, 12-14 days before 'Flordaking' and 'Texking'.

*Flower type*.—Showy.

*Flower size*.—Flower diameter at full bloom is approximately 36 to 38 mm. The length of the flower at the pink bud stage before opening ranges from 15 to 18 mm.

*Bloom quantity*.—Considered abundant.

*Flower bud frequency*.—Normally 1 to 2 per node.

*Petal size*.—

*General*.—Considered medium to medium large for the species.

*Width*.—Approximately 12 to 15 mm.

*Length*.—Approximately 16 to 18 mm.

*Petal form*.—Broadly ovate.

*Petal count*.—Nearly always 5.

*Petal color*.—Light pink when young (RHS Red-Purple Group 62C, 69A, 73D and Purple Group 75C-D).

*Petal claw*.—

*Form*.—The claw is considered truncate in shape and has a medium size when compared to other varieties.

*Length*.—Approximately 1 to 2 mm.

*Width*.—Approximately 1 mm.

*Petal margins*.—Generally considered variable, from nearly smooth to slightly undulate.

*Petal apex*.—Generally — The petal apices appear slightly domed.

*Flower pedicel*.—

*Length*.—Considered present, and having an average length of approximately 2 mm.

*Thickness*.—Considered average, approximately 1 mm.

*Color*.—A light green (Yellow-Green Group N144D and 145C-D).

*Floral nectaries*.—

*Color*.—Light yellow (Yellow Group 3A-C and 4A-B).

*Hypanthium*.—

*Surface texture*.—Generally glabrous

*Color*.—Maroon with green (approximately Yellow-Green Group N144D and 145C-D, Greyed-Red Group 181A-B, 183A-C, Greyed-Purple Group 184A-B and 185A).

*Sepals*.—

*Surface texture*.—The surface has a short, fine, and wooly texture.

*Size*.—Average, and ovate in form. Sepals range from 5.4 to 7.5 mm in length and 3.3 to 5.4 mm in width at the pink bud stage depending on the stage of development.

*Color*.—A dull maroon with green (approximately Yellow-Green Group N144D and 145C-D, Greyed-Red Group 181A-B, 183A-C, Greyed-Purple Group 184A-B and 185A).

*Anthers*.—

*General*.—Average in size for the species.

*Anther size*.—generally approximately 1.0 mm in length and approximately 0.5 mm in width.

*Color*.—Yellow (approximately Yellow Group 8A-B and 9A-B).

*Pollen production*.—Pollen is abundant, and is a yellow color. Approximately Yellow Group 13A-C and Yellow-Orange Group 14C-D.

*Filaments*.—Size — Variable in length, approximately 11 to 14 mm, with the filaments equal to or slightly shorter than the pistil. The stamens are generally below the pistil and do not protrude when the flowers are at the pink bud stage of development.

*Color*.—White (approximately White Group N999D).

*Pistil*.—

*General*.—Average in size, but slightly longer or equal to the general anther height.

*Length*.—Approximately 16 to 18 mm, including the ovary. The stigma is generally above the stamens at the pink bud stage of flower development.

*Color*.—Considered white when young (approximately White Group 155A-D and N999D).

*Pubescence*.—Absent, the pistil including the ovary is not pubescent.

Fruit:

*Maturity when described*.—The present variety of fruit is described, as it would be found in its firm ripe condition at full commercial maturity in early to mid May in the medium chill zone of Texas. 'Smooth Zest One' ripens with or slightly before 'Flordaking' and 5-6 days before 'Smooth Delight One' and 'Smooth Delight Two' in the medium chill zone.

*Size*.—General — Medium to medium large for the season and considered uniform.

*Average cheek diameter*.—Approximately 63 to 66 mm.

*Average suture diameter*.—Approximately 59 to 63 mm.

*Average axial diameter*.—Approximately 58 to 64 mm.

*Fruit form*.—Generally considered ovate and truncate.

*Fruit suture*.—Generally, the suture appears as a thin line/indentation that extends from the base to the apex, and appears deeper at the apex. No apparent callusing or stitching exists along the suture line.

*Color*.—Medium red (Orange-Red Group N34A-B).

*Ventral surface*.—Form — Considered uniform.

*Stem cavity*.—Size — Considered moderately shallow to medium for the species.

*Length*.—Approximately 17 to 20 mm.

*Width*.—Approximately 14 to 15 mm.

*Depth*.—Approximately 9 to 12 mm.

*Fruit base*.—Flat.

*Fruit apex*.—Flat and round.

*Fruit stem*.—Length — 12 to 13 mm. Thickness — 2 to 4 mm. Color — Yellow-Green Group 144A-C.

*Fruit skin*.—Generally considered medium or average in thickness. Surface Texture — Smooth. Skin Acidity — Considered neutral. Tenacious to Flesh — Yes at commercial maturity. Tendency to Crack — Occasional tip cracking observed. Skin Color — Generally — Variable, with a large percentage (approximately 90%) of the fruit surface covered with an attractive blush as described under Blush Color. Pubescence — Absent. The skin has medium glossiness. Blush Color — The blush color ranges from red (Red Group 45A-B) to orange (Orange-Red Group 33A) with many degrees of shading and blending. Skin Ground Color — Yellow Group 6A-B.

*Flesh color*.—White Group 155B and N999D with red appearing near the skin (Greyed-Purple Group 186A-D).

*Stone cavity color*.—White Group 155B.

*Flesh texture*.—Generally, the flesh is considered firm at commercial maturity.

*Ripening*.—Generally the fruit of the present variety ripens evenly.

*Flavor*.—Considered sweet with an acidic flavor.

*Aroma*.—Pleasant and reasonably abundant.

*Eating*.—Generally considered very good, particularly for an early ripening variety.

Stone:

*Attachment*.—Clingstone (strongly adherent) at commercial maturity.

*Stone size*.—Generally considered medium relative to the ratio of stone to fruit size.

*Length*.—Approximately 28 to 34 mm.

*Width*.—Approximately 23 to 25 mm.

*Thickness*.—Approximately 16 to 20 mm.

*Fibers*.—Generally a few medium length fibers are attached along the entire surface of the stone.

*Stone form*.—Generally the stone is considered Ovate to Obovate.

*Stone base angle*.—The stone is medium to wide.

*Apex shape*.—The stone apex varies from medium to wide.

*Stone shape*.—The stone is normally ovoid.

*Stone surface*.—

*Surface texture*.—Minor surface markings are honeycombed with numerous single pit and chains of pits.

*Ridges*.—A few ridges are present basally, and converge towards the base of the stone.

*Ventral edge*.—Width — Considered large with some truncation.

*Dorsal edge*.—Shape — Grooved and having moderately rough edges.

*Stone color*.—The color of the dry stone is light brown (161A-B of the Greyed-Yellow Group and 164B-C and 165C of the Greyed-Orange Group). The color of the inside surface of the endocarp is primarily 158A-B of the Yellow-White Group, 159A-B of the Orange-White Group, 161C-D of the Greyed-Yellow Group and 164D and 165D of the Greyed-Orange Group.

*Tendency to split*.—Splitting is relatively uncommon.

*Kernel*.—The kernel fills the endocarp at harvest and measures approximately 3-5 mm in thickness, 10-12 mm in width, and 15-19 mm in length. When dried the shriveled kernels measure approximately 1-3 mm in thickness, 9-10 mm in width, and 15-16 mm in length. The colors of the shriveled kernels are primarily Greyed-Orange Group 165A-B.

*Use*.—The subject variety, 'Smooth Zest One', is considered to be a nectarine tree of early-season maturity, which produces fruit which are firm, attractively colored, and which are useful for both local and regional fresh fruit markets.

*Keeping quality*.—Good.

*Resistance to insects and disease*.—No particular susceptibilities or resistances were noted or are claimed.

*Shipping quality*.—Average.

Although the new variety of nectarine tree possesses the described characteristics when grown under the ecological conditions prevailing in the low to medium chill zone of Texas, it will be understood that variations of the usual magnitude and characteristics incident to the changes in growing conditions, fertilization, pruning, and pest control are to be expected.

REFERENCES

Andrews, C. P., W. B. Sherman, and P. M. Lyrene. 1979. 'Flordaking' peach. HortScience 14:81-82.

Anon. 2001. RHS Colour Chart. The Royal Hort. Soc., London.

Brooks, R. M. and H. P. Olmo. 1997. Register of New Fruit and Nut Varieties. 3rd Edition. American Society of Horticultural Science Press, Alexandria, Va.

Byrne, D. H. and N. Anderson. 2013. TexFirst, an Early-ripening, low chill peach for the subtropics. HortScience 47(2):1803-1804. U.S. Plant Pat. No. 26,119.

Byrne, D. H and N. Anderson. Nectarine tree, Smooth Delight One. U.S. Plant patent application Ser. No. 14/544,508.

Byrne, D. H and N. Anderson. Nectarine tree, Smooth Delight Two. U.S. Plant patent application Ser. No. 14/544,522.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

We claim:

1. A new and distinct *Prunus persica* tree, substantially as illustrated and described herein.

* * * * *